(12) United States Patent
Ramachandran et al.

(10) Patent No.: US 10,815,167 B2
(45) Date of Patent: Oct. 27, 2020

(54) OLEFIN DOUBLE BOND ISOMERIZATION CATALYST WITH HIGH POISON RESISTANCE

(71) Applicant: Lummus Technology Inc., Bloomfield, NJ (US)

(72) Inventors: Bala Ramachandran, Easton, PA (US); Sukwon Choi, Clifton, NJ (US); Robert J. Gartside, Brewster, MA (US)

(73) Assignee: Lummus Technology Inc., Bloomfield, NJ (US)

( * ) Notice: Subject to any disclaimer, the term of this patent is extended or adjusted under 35 U.S.C. 154(b) by 149 days.

(21) Appl. No.: 15/985,242

(22) Filed: May 21, 2018

(65) Prior Publication Data

US 2018/0273443 A1    Sep. 27, 2018

Related U.S. Application Data

(62) Division of application No. 14/548,460, filed on Nov. 20, 2014, now Pat. No. 9,975,819.

(Continued)

(51) Int. Cl.
*C07C 5/25* (2006.01)
*C07C 1/24* (2006.01)
(Continued)

(52) U.S. Cl.
CPC ............. *C07C 5/2512* (2013.01); *B01J 21/04* (2013.01); *B01J 21/063* (2013.01);
(Continued)

(58) Field of Classification Search
CPC ................................. B01J 21/063; B01J 21/04
(Continued)

(56) References Cited

U.S. PATENT DOCUMENTS 2,976,299 A * 3/1961 Manly ................. C07D 309/18
549/356
3,079,447 A * 2/1963 Bartlett .................. C07C 5/367
585/252

(Continued)

FOREIGN PATENT DOCUMENTS

JP       06-192140       7/1994
WO       0071253         11/2000
(Continued)

OTHER PUBLICATIONS

Dong Yanmin et al., "Synthesis of methyl propyl carbonate via gas-phase transesterification over TiO2/Al2O3." Journal of Molecular Catalysis A: Chemical 331, pp. 125-129. (Year: 2010).*

(Continued)

*Primary Examiner* — Patricia L. Hailey
(74) *Attorney, Agent, or Firm* — Osha Liang LLP

(57) ABSTRACT

A process for the double-bond isomerization of olefins is disclosed. The process may include contacting a hydrocarbon stream including olefins with a γ-alumina-titania isomerization catalyst to convert at least a portion of the olefin to its positional isomer. The γ-alumina-titanic isomerization catalysts disclosed herein may also have the activity to convert alcohol into additional olefins, while having increased resistance to oxygenate poisons.

17 Claims, 5 Drawing Sheets

Related U.S. Application Data

(60) Provisional application No. 61/906,618, filed on Nov. 20, 2013.

(51) Int. Cl.
*C07C 6/04* (2006.01)
*B01J 21/06* (2006.01)
*B01J 21/04* (2006.01)
*B01J 35/10* (2006.01)

(52) U.S. Cl.
CPC ............ *B01J 35/1019* (2013.01); *C07C 1/24* (2013.01); *C07C 6/04* (2013.01); *C07C 2521/04* (2013.01); *C07C 2521/06* (2013.01); *Y02P 20/52* (2015.11)

(58) Field of Classification Search
USPC ......... 502/351; 422/600, 630; 585/332, 477, 585/480, 664, 734, 750
See application file for complete search history.

(56) References Cited

U.S. PATENT DOCUMENTS

| | | | | |
|---|---|---|---|---|
| 3,261,879 | A * | 7/1966 | Banks ..................... | C07C 6/04 585/643 |
| 3,565,829 | A * | 2/1971 | Friedrichsen et al. ..................... | B01J 21/063 502/344 |
| 3,663,636 | A * | 5/1972 | Suggitt et al. ........... | B01J 23/28 585/470 |
| 4,593,014 | A * | 6/1986 | Halluin ................... | B01J 23/40 502/242 |
| 5,098,876 | A * | 3/1992 | Lin .......................... | B01J 23/28 502/156 |
| 5,962,367 | A * | 10/1999 | Shen ....................... | B01J 21/063 502/302 |
| 7,501,379 | B2 * | 3/2009 | Ignatchenko ............ | B01J 23/02 502/351 |
| 8,399,376 | B2 * | 3/2013 | Dien-Barataud ..... | C04B 35/478 423/259 |
| 9,061,265 | B2 * | 6/2015 | Seki ....................... | B01J 21/063 |
| 2009/0186953 | A1 * | 7/2009 | Gesenhues ............... | B01J 37/03 518/728 |
| 2010/0221166 | A1 * | 9/2010 | Muggli ................... | B01D 53/83 423/245.1 |
| 2011/0263917 | A1 * | 10/2011 | Van Hal .................. | C07C 5/417 585/322 |
| 2013/0245348 | A1 * | 9/2013 | Vermeiren ............ | C07C 5/2708 585/324 |
| 2015/0141706 | A1 * | 5/2015 | Choi ........................ | C07C 7/04 568/697 |
| 2015/0141721 | A1 * | 5/2015 | Choi ....................... | B01J 8/0453 585/315 |
| 2017/0165640 | A1 * | 6/2017 | Castillo Cervantes ..................... | B01J 35/002 |

FOREIGN PATENT DOCUMENTS

| | | |
|---|---|---|
| WO | 0121304 | 3/2001 |
| WO | 0132590 | 5/2001 |
| WO | 2011043995 | 4/2011 |
| WO | 2012027948 | 3/2012 |

OTHER PUBLICATIONS

Emmanuel Lecrenay et al., "Hydrodesulfurization activity of CoMo and NiMo supported on Al2O3-TiO2 for some model compounds and gas oils." Applied Catalysis B: Environmental 18, pp. 325-330. (Year: 1998).*
Kuo-Tseng Li et al., "Esterification of lactic acid over TiO2-Al2O3 catalysts." Applied Catalysis A: General 433-434, pp. 275-279. (Year: 2012).*
C. Pophal et al., "Hydrodesulfurization of dibenzothiophene derivatives over TiO2-Al2O3 supported sulfided molybdenum catalyst." Catalysis Today 39, pp. 21-32. (Year: 1997).*
T. Klimova et al., "Tuning of textural and structural characteristics of Al2O3-TiO2 mixed oxide supports." Studies in Surface Science and Catalysis, vol. 118, pp. 807-815. (Year: 1998).*
Office Action issued in corresponding Singaporean Application No. 11201603879R dated Oct. 2, 2018 (7 pages).
International Search Report and Written Opinion dated Mar. 12, 2015 in corresponding International Application No. PCT/US2014/066404 (10 pages).
Office Action dated Jul. 23, 2015 in corresponding Taiwan application No. 103140224 (7 pages).
First Office Action dated Nov. 3, 2016 in corresponding Chinese application No. 201480062300.0 (w/translation) (9 pages).
"Conversion of ethanol and isopropanol on alumina, titania and alumina-titania catalysts"; M.R. Mostafa et al.; Material Letters 12 (1991) 207-213 (7 pages).
Written Opinion dated Mar. 13, 2017 in corresponding Singapore application No. 11201603879R (7 pages).
Extended European Search Report issued in corresponding European Application No. 14864489.1 dated Apr. 21, 2017 (13 pages).
Office Action issued in corresponding Japanese Application No. 2016-533571 with English translation dated May 30, 2017 (11 pages).
Third Office Action dated Sep. 4, 2017 in corresponding Chinese application No. 201480062300.0 (w/translation) (12 pages).
Office Action issued in corresponding GCC Patent Office Application No. GC 2014-28348 dated Aug. 8, 2017, and English translation thereof (4 pages).
Office Action issued in corresponding CN Application No. 201480062300.0 with partial English translation dated Feb. 5, 2018 (7 pages).
Office Action issued in corresponding EP Application No. 14864489.1 dated Mar. 2, 2018 (6 pages).
Written Opinion issued in corresponding SG Application No. 11201603879R dated Feb. 26, 2018 (7 pages).
Hubert et al. The Isomerization of Olefins Part II. Thermal and Catalytic Isomerization of Olefins using Acids, Metals, Metal Complexes, or Boron Compounds as Catalysts, Synthesis, 1970, pp. 405-430.
Lemberton et al, Mechanisms of Isomerization of Butenes on Titanium Dioxide, J.C.S. Chem. Comm., 1799, pp. 883-884.

* cited by examiner

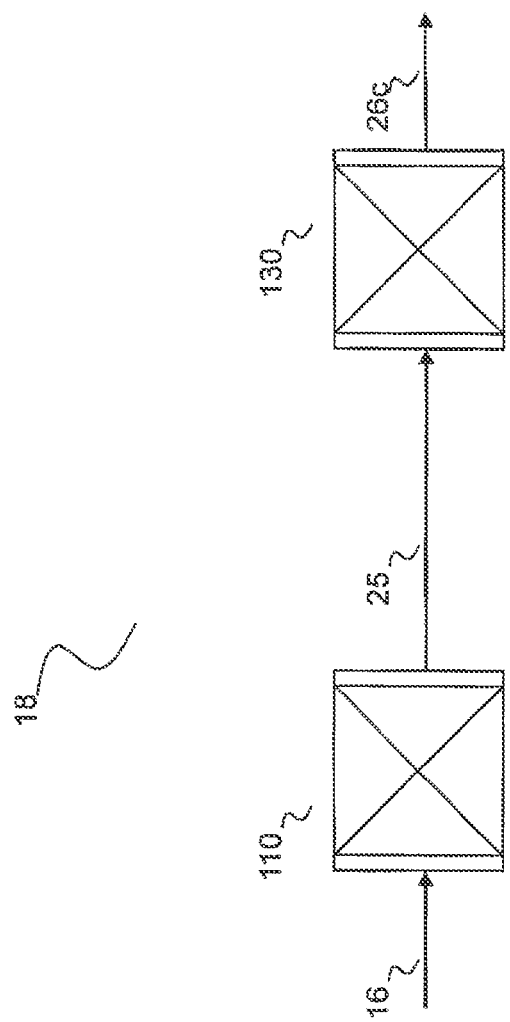

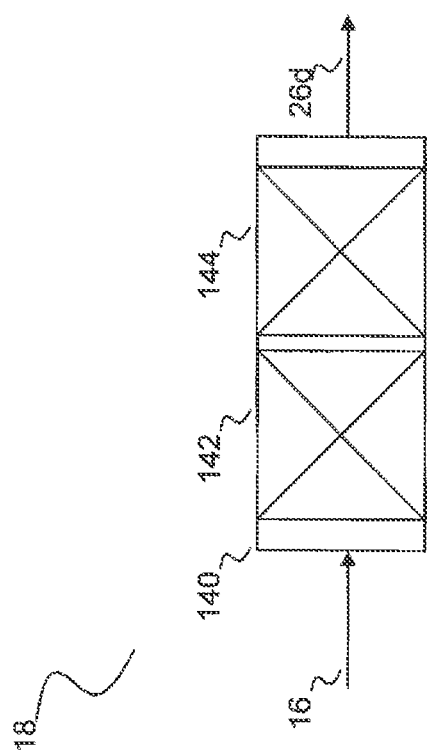

US 10,815,167 B2

OLEFIN DOUBLE BOND ISOMERIZATION CATALYST WITH HIGH POISON RESISTANCE

FIELD OF THE DISCLOSURE

Embodiments disclosed herein relate generally to the processing of olefinic hydrocarbons from a cracking process, such as steam or fluid catalytic cracking, for conversion of one olefin into a second olefin via isomerization and/or metathesis.

BACKGROUND

In typical olefin plants, such as illustrated in U.S. Pat. No. 7,223,895, there is a front-end demethanizer for the removal of methane and hydrogen followed by a deethanizer for the removal of ethane, ethylene and $C_2$ acetylene. The bottoms from this deethanizer tower consist of a mixture of compounds, including olefins, ranging in carbon number from $C_3$ to $C_6$. This mixture may be separated into different carbon numbers, typically by fractionation. Once separated, the $C_3$-$C_6$ olefins may undergo isomerization and metathesis to produce a desired product.

The metathesis catalysts and the double bond isomerization catalysts used are generally quite sensitive to poisons. Poisons include water, $CO_2$, and oxygenates, such as ethers and alcohols. It is common practice to employ guard beds upstream of the isomerization/metathesis reaction system to insure the removal of these poisons. In practice these guard beds are either directly before the metathesis reaction system or further upstream.

Double-bond isomerization catalysts, such as magnesium oxide, are currently commercially used in the form of tablets having an effective diameter of about 5 mm. As used herein, effective diameter refers to the diameter that non-spherical shaped particles would have if it were molded into a sphere. These tablets exhibit good isomerization activity when processing butenes alone. However, such tablets exhibit activity for isomerization of 1-butene to 2-butene only fur a short time in the presence of poisons. Further, their performance is progressively worse as the number of reaction cycles increase. After several regeneration/reaction cycles, their activity for isomerization is low. This performance shortfall may lead to a rapid buildup of 1-butene in the system over time, limiting reactor performance by hydraulically limiting the recycle, and limiting the overall conversion of butenes to propylene or other end products that can be obtained economically. A similar loss of activity is experienced when operating these catalysts as double bond isomerization catalysts alone for the production of the terminal olefin from the interior olefin.

Some attempts have been made to improve the performance of magnesium oxide catalysts. For example, U.S. Pat. No. 6,875,901 discloses improvements to the deactivation rate of magnesium oxide isomerization catalysts by limiting certain impurities, such as phosphorous, sulfur, transition metals, etc. Deactivation in the presence of oxygenates, however, remains problematic.

SUMMARY OF THE CLAIMED EMBODIMENTS

Catalysts have now been found that may be used in isomerization and/or combined isomerization/metathesis processes that are tolerant to poisons that may be present in the feed, including oxygenates.

In one aspect, embodiments disclosed herein relate to a process for the double-bond isomerization of olefins, the process including: contacting a fluid stream comprising olefins with a fixed bed comprising an isomerization catalyst, that is tolerant to oxygenate poisons, to convert at least a portion of the olefin to its isomer.

In another aspect, embodiments disclosed herein relate to a process for the double-bond isomerization of olefins, and simultaneous dehydration of alcohols. The simultaneous isomerization and dehydration may occur with a single catalyst and may occur in one or more reactors or reactor beds.

In another aspect, embodiments disclosed herein relate to a process for the production of propylene, including: fractionating a hydrocarbon stream comprising n-butenes, isobutene, paraffins, and alcohols into at least two fractions including a light $C_4$ fraction comprising isobutene and a heavy $C_4$ fraction comprising n-butenes and paraffins; feeding ethylene and the heavy $C_4$ fraction to a fixed bed reactor comprising a metathesis catalyst and an isomerization catalyst, that is tolerant to oxygenate poisons, contacting the heavy $C_4$ fraction with the isomerization catalyst to convert at least a portion of the 1-butene to 2-butene while converting at least a portion of alcohols into additional olefins; and contacting ethylene and at least a portion of the 2-butene with a metathesis catalyst to form a metathesis product comprising propylene, paraffins, any unreacted ethylene, any unreacted alcohols, and any unreacted 1-butene and 2-butene.

Other aspects and advantages will be apparent from the following description and the appended claims.

BRIEF DESCRIPTION OF DRAWINGS

FIG. 4 is a simplified process flow diagram of a process for isomerization and metathesis using catalysts according to embodiments disclosed herein.

FIG. 5 is a simplified process flow diagram of a process for isomerization and metathesis using catalysts according to embodiments disclosed herein.

DETAILED DESCRIPTION

Figure 1:
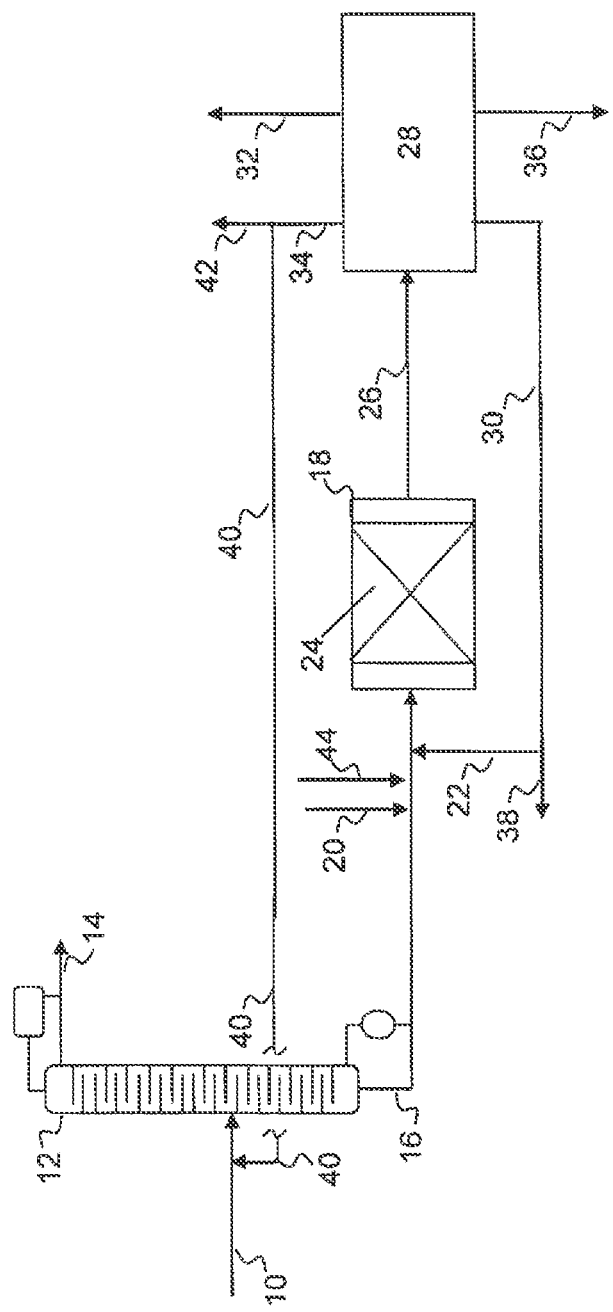
FIG. 1 is a simplified process flow diagram of a process for isomerization and metathesis using catalysts according to embodiments disclosed herein.

Embodiments disclosed herein provide an alumina-based isomerization catalyst that exhibits little or no oxygenate poisoning. The catalyst may be a γ-alumina-titania crystalline mixture including active sites that catalyze the positional isomerization of olefins. In some embodiments, the alumina-titanic catalyst may have a composition of titanium with a lower limit of 0.01, 1, 2, 3, 4, 5, 10, 15, 20, or 25 to an upper limit of 15, 20, 25, 30, 35, 40, 45, or 50 wt %, where any lower limit may be combined with any upper limit. Other aspects of the γ-alumina-titania catalyst are described below.

γ-Alumina-titania catalysts herein may also have active sites for catalyzing the dehydration of alcohols. That is, the catalyst may have a dual activity that allows the catalyst to dehydrate alcohols, producing additional olefins, as well as facilitating the double bond isomerization of the olefins. While certain aspects will be described herein in terms of the alumina-titania catalysts, it should be understood that various other dual activity catalysts are also contemplated as being within the scope of embodiments disclosed herein.

As described herein, the alumina-titania catalyst being used for the dual purpose of double bond isomerization and alcohol dehydration is an improvement upon traditional basic metal oxide catalysts because it does not lose activity in the presence of oxygenates, such as ethers, alcohols, and water. Additionally, it has been found to increase in activity in the presence of about 5 ppm methanol and achieves a more desirable positional olefin equilibrium ratio, and the alumina catalyst described herein does not lose surface area during high temperature catalyst regeneration.

The γ-alumina-titanic catalyst described herein may be used alone or in a mixture with traditional MgO catalyst.

The isomerization catalysts according to embodiments disclosed herein may be in the form of pellets, extrudates, and the like. While powders are mentioned as a useful catalyst form in U.S. Pat. No. 6,875,901, because of high pressure drops associated with use of powders in fixed or packed beds, powders are not commercially used when isomerization catalysts are admixed with metathesis catalysts and used in the presence of ethylene in commercial fixed bed reactors or in fixed bed isomerization reactors. Accordingly, powders and finer material not typically used in a fixed bed reactor are specifically excluded from catalysts according to embodiments disclosed herein.

The isomerization catalysts according to embodiments disclosed herein are those that may be used with fixed bed reactors or formed as catalytic distillation structures, and thus isomerization catalysts are in the form of pellets, spheres, extrudates, and the like, and will typically have an effective diameter of 0.5 mm to 5 mm, such as in the range from 1 mm to 4 mm, or in the range from 2 mm to 3 mm.

Double-bond isomerization catalysts disclosed herein may be used for the conversion of various internal olefins, such as 2-butene, to an alpha-olefinic compound, such as 1-butene, in fixed bed reactors, distillation column reactors, and other reactors known in the art. While described below with respect to butenes, conversion of 2-pentene to 1-pentene, 2- or 3-hexene to 1-hexene, 2- or 3-heptene to 1-heptene, and the like are also contemplated.

In other embodiments disclosed herein, double-bond isomerization catalysts may also be used to for the conversion of alpha-olefins to internal olefins. In particular, catalysts according to embodiments disclosed herein are useful in processes for the concurrent isomerization of 1-butene to 2-butene, dehydration of alcohol to foray addition olefins, and metathesis of 2-butene with ethylene to form propylene, where the isomerization reaction may be performed in the presence of ethylene.

According to one or more embodiments disclosed herein, a process for the isomerization of olefins may include contacting a mixed C4 stream, or mixture of olefins, with a γ-alumina-titania catalyst in a reaction zone. The mixture may include, for example, 1-butene, 2-butene, oxygenates, and other compounds. The γ-alumina-titania catalysts disclosed herein, in some embodiments, may have an activity for the simultaneous dehydration of the alcohols to form olefins and water, and isomerization of the resulting olefins and feedstock olefins to form an isomerization product containing mono-olefinic hydrocarbons.

The catalyst according to embodiments disclosed herein, is a γ-alumina-titania catalyst with a surface area in some embodiments greater than 200 m^2/g, in other embodiments greater than 250 m^2/g, in other embodiments greater than 300 m^2/g, in other embodiments greater than 350 m^2/g, and in other embodiments greater than 400 m^2/g.

The γ-alumina-titania catalyst, while having dual activity for the dehydration of alcohols and the double bond isomerization of olefins, may also exhibit a resistance to typical oxygenate poisons up to a concentration of 1000 ppm in some embodiments; such as oxygenate poisons in the range of 10 ppm to 900 ppm, in other embodiments 100 ppm to 800 ppm.

Additionally, the γ-alumina-titania catalyst may also form an initial bed in the reaction zone, such as upstream of or in admixture with a conventional isomerization catalyst, such as upstream of a bed of MgO catalysts, a γ-alumina-titania/MgO catalyst mixture, a mixture of basic metal oxide isomerization catalyst and a metathesis catalyst, or upstream of a metathesis catalyst bed. Isomerization catalysts that may be used in beds downstream of the γ-alumina-titania catalysts herein may include basic metal oxides such as magnesium oxide, calcium oxide, barium oxide, strontium oxide, and lithium oxide, either individually or in combination. Other oxides, such as sodium oxide or potassium oxide may be incorporated into the catalyst as promoters.

Basic metal oxide isomerization catalysts, such as MgO, are generally sensitive to oxygenate poisons. Using an initial γ-alumina-titania catalyst bed may advantageously provide poison scavenging capabilities as well as initial isomerization of olefins; in some embodiments, the catalyst may also provide for dehydration of alcohols into additional olefins.

The double bond isomerization reactions disclosed herein may be carried out in a temperature range from 5° C. to about 500° C., such as at a temperature in the range from 250° C. to about 450° C. The reaction may also be controlled at a pressure in the range from atmospheric pressure to about 2000 psig, such as atmospheric to 1500 psig, or atmospheric to 700 psig. The reaction may also be controlled from about 50 psig or 100 psig to about 500 psig. The pressurization may also optionally be under an inert atmosphere.

The γ-alumina-titanic catalysts disclosed herein may be used in a process for the production of olefins. The process may advantageously utilize an isomerization catalyst having a dual activity for dehydration of alcohols and isomerization of olefinic double bonds. In conjunction with a metathesis catalyst, either in admixture or in a downstream reaction bed, the isomerization and metathesis catalysts may be used to produce desired olefins from a mixture of olefins.

The metathesis catalyst disclosed herein can be any known metathesis catalyst that has an activity to react one olefin with another olefin, which may be the same or different, to produce a third and fourth olefin, which may be the same or different.

The metathesis catalyst may be admixed with the isomerization catalyst, may be a separate layer in the same bed, may be a separate bed in the same reactor, or may be in a separate reactor.

The γ-alumina-titanic isomerization catalyst may form a guard bed upstream of a bed including a mixture of isomerization and metathesis catalyst, may be admixed with a basic metal oxide isomerization catalyst separate from the metathesis catalyst, or may be admixed with a basic metal oxide isomerization/metathesis catalyst.

In some embodiments, a feedstock for processes disclosed herein is a mixed C4 stream containing 1-butene and 2-butene, which may contain other C4 hydrocarbons and oxygenates, such as butanols. Optionally, a second feed stream of C2 to C6 alcohols may be fed to the reaction zone, When present, the alcohols are dehydrated by the γ-aluminatitania catalyst to produce additional olefins. The olefins present, as well as those produced in situ are isomerized to produce an isomerization product containing 2-butene. The 2-butene may then be metathesized with ethylene to produce propylene.

The oxygenate tolerance and activity for dehydration of alcohols to form additional olefins of γ-alumina-titania catalysts herein may provide for several useful permutations. According to embodiments disclosed herein, ethanol may be dehydrated to form ethylene which can be metathesized with 2-butene to produce propylene. This may be useful, for example, where ethanol supplies are available but ethylene is of limited availability. According to another embodiment, propanol may be dehydrated to form additional propylene product. According to yet another embodiment, iso-, 1-, or 2-butanol may be dehydrated to form additional 1- and 2-butene. A combination of these embodiments is also contemplated by this disclosure.

According to one or more embodiments herein, a mixed $C_4$ feed disclosed herein may include $C_3$ to $C_{6+}$ hydrocarbons, including $C_4$, $C_4$ to $C_5$, and $C_4$ to $C_6$ cracker effluents, such as from a steam cracker or a fluid catalytic cracking (FCC) unit. Other refinery hydrocarbon streams containing a mixture of $C_4$ olefins may also be used. When $C_3$, $C_5$ and/or $C_6$ components are present in the feed, the stream may be pre-fractionated to result in a primary $C_4$ cut, a $C_4$ to $C_5$ cut, or a $C_4$ to $C_6$ cut.

$C_4$ components contained in the feed stream may include n-butane, isobutane, isobutene, 1-butene, 2-butene, and butadiene, In some embodiments, the mixed $C_4$ feed is pretreated to provide a normal-butene-rich feed for the metathesis reaction. For example, when butadiene is present in the $C_4$ feed, the butadiene may be removed via hydrogenation or extraction. In other embodiments, the mixed butenes feed following or in conjunction with butadiene hydrogenation may be subjected to hydroisomerization conditions to convert 1-butene to 2-butene, with isobutene being separated from a 2-butene stream by fractionation.

In some embodiments, as alluded to above, ethylene and a hydrocarbon mixture including normal butenes may be fed to a reactor containing catalysts having both a metathesis functionality and an isomerization functionality, to convert at least a portion of the 1-butene to 2-butene, and to react the 2-butene with ethylene to form propylene as a metathesis product. The ethylene may be fed to the reactor at a rate to maintain a ratio of ethylene to n-butenes of at least 0.5; at least 1.0 in other embodiments; in the range from 0.5 to about 2.5 in other embodiments; and from about 1.0 or 1.5 to about 2.0 in yet other embodiments. The catalyst contained within the metathesis reactor may be any known metathesis catalyst, including oxides of Group VI B and Group VII B metals on supports. Catalyst supports can be of any type and could include alumina, silica, mixtures thereof, zirconia, and zeolites. In addition to the metathesis catalyst, the catalyst contained in the metathesis reactor may include a dual activity dehydration and double bond isomerization γ-alumina-titania catalyst, as described above.

An example of a metathesis process for which catalysts according to embodiments disclosed herein may be useful is illustrated in FIG. 1. A mixed hydrocarbon stream, such as a $C_4$ cut containing n-butenes and paraffins may be fed to an inlet via flow line 10 to a separator 12, where the $C_4$ cut may be separated into at least two fractions, including a light fraction, which may contain any light C4's and C3's contained in the C4 cut, and a heavy $C_4$ fraction, including n-butenes. The light fraction may be recovered from separator 12 as an overheads fraction via flow line 14.

The heavy $C_4$ fraction may be recovered as a bottoms fraction via flow line 16 and fed to an isomerization/metathesis reactor(s) 18. Ethylene may be co-fed to reactor (s) 18 via flow lines 20 and/or 22. Isomerization me reactor (s) 18 may contain one or more beds 24 of a conventional metathesis catalyst and γ-alumina-titania isomerization catalysts according to embodiments disclosed herein. The metathesis and isomerization catalysts may be admixed in a single bed or may be placed in the reactor in series, as disclosed below, such as by loading the catalysts sequentially in a single bed or placing the catalysts in the reactor as separate beds.

Effluent from isomerization/metathesis reactor(s) 18 may be recovered via an outlet and fed via flow line 26 to a separation system 28, which may include, for example, distillation apparatus for separating the effluent into carbon number groups. As illustrated, separation system 28 may fractionate the metathesis product into at least four fractions, including an ethylene-containing fraction recovered via flow line 30, a propylene-containing fraction recovered via flow line 32, a $C_4$ fraction recovered via flow line 34, and a $C_{5+}$ fraction recovered via flow line 36.

A portion of the $C_2$ fraction recovered via flow line 30 may be purged from the system via flow line 38. If desired, at least a portion of the ethylene recovered via flow line 30 may be recycled as ethylene feed via flow line 22 to isomerization/metathesis reactor(s) 18.

At least a portion of the $C_4$ fraction recovered via flow line 34 may be recycled to separator 12 via flow line 40, and a portion may be purged, if necessary, via flow line 42. Although not illustrated, the $C_4$ fraction recovered via flow line 34 may alternatively be recycled to metathesis reactor 18 or to alternative downstream processing units. Additionally, when the hydrocarbon stream contains butadiene, the process may include a hydrogenation stage to hydrogenate at least a portion of the butadienes prior to fractionating the hydrocarbon feed in separator 12.

Figure 2:
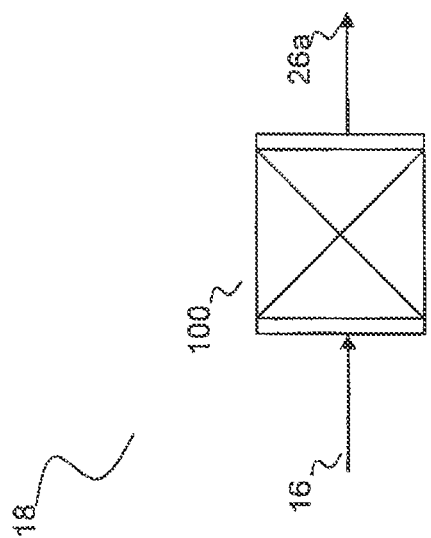
FIG. 2 is a simplified process flow diagram of a process for isomerization and metathesis using catalysts according to embodiments disclosed herein.

Another example of a process for which catalysts according to embodiments disclosed herein may be useful is illustrated in FIG. 2. Isomerization/metathesis reactor system(s) 18 may include an isomerization reactor 100 containing a γ-alumina-titania isomerization catalyst according to embodiments disclosed herein. Isomerization reactor 100 may contain the γ-alumina catalyst as disclosed herein, and in some embodiments may have activity for the dehydration of alcohols and the double bond isomerization of olefins, and also exhibit a resistant to typical oxygenate poisons. Isomerized effluent 26a may then be further processed and/or separated downstream, such as by methods discussed above.

Figure 3:
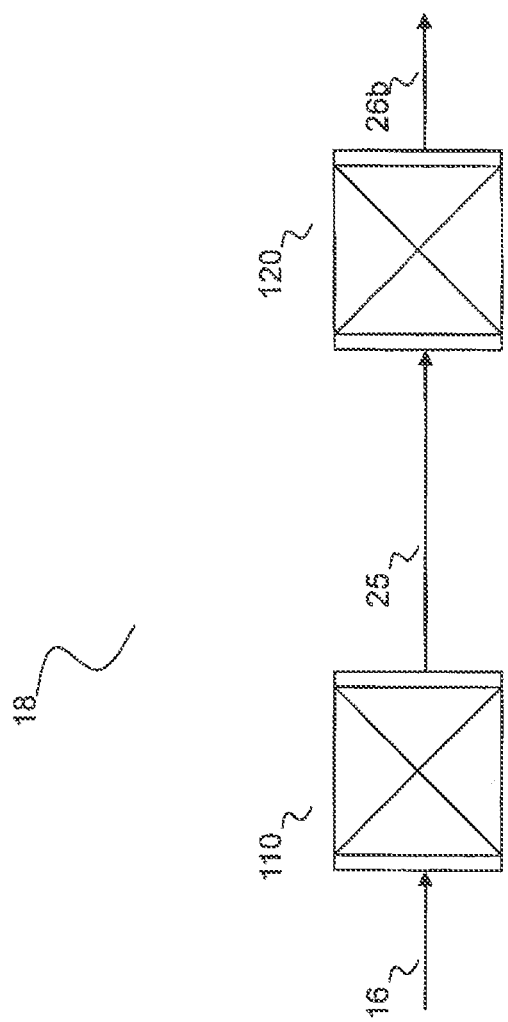
FIG. 3 is a simplified process flow diagram of a process for isomerization and metathesis using catalysts according to embodiments disclosed herein.

Another example of a process for which catalysts according to embodiments disclosed herein may be useful is illustrated in FIG. 3. Isomerization/metathesis reactor system(s) 18 may include an isomerization reactor 110 containing an isomerization catalysts according to embodiments disclosed herein. Reactor 120 may contain an isomerization catalyst according to embodiments disclosed herein, or any conventional isomerization catalyst, and may also contain any conventional metathesis catalyst. The metathesis and isomerization catalysts in reactor 120 may be admixed in a single bed or may be placed in the reactor in series, such as by loading the catalysts sequentially in a single bed or placing the catalysts in the reactor as separate beds.

Isomerization reactor 110 may contain the γ-alumina-titania catalysts as disclosed herein, including those that may have activity for the dehydration of alcohols and the double bond isomerization of olefins, and also exhibit a resistant to typical oxygenate poisons. Isomerized effluent 25 may be fed to reactor 120 for additional isomerization and metathesis. Metathesized effluent 26b may then be separated downstream, such as discussed above with respect to FIG. 1.

Another example of a process for which catalysts according to embodiments disclosed herein may be useful is illustrated in FIG. 4. Isomerization/metathesis reactor system(s) 18 may contain isomerization reactor 110 with an isomerization catalysts according to embodiments disclosed herein. Reactor 130 may contain any conventional metathesis catalyst. The metathesis catalyst of reactor 130 may be a single bed or may be placed in the reactor in multiple beds.

Isomerization reactor 110 may contain the γ-alumina-titania catalyst as disclosed herein. Isomerized effluent 25 may be fed to reactor 130 for olefin metathesis. Metathesized effluent 26c may then be separated downstream, as described above with respect to FIG. 1. In some embodiments, an intermediate water separation step may be used between reactors 120 and 130.

Another example of a process for which catalysts according to embodiments disclosed herein may be useful is illustrated in FIG. 5. Isomerization/metathesis reactor system(s) 18 may contain isomerization reactor 140 with an isomerization catalyst 142 according to embodiments disclosed herein. Reactor 140 may also contain an isomerization catalyst 144 according to embodiments disclosed herein, or any conventional isomerization catalyst, and may also contain any conventional metathesis catalyst. The metathesis and isomerization catalysts in catalyst bed 144 may be admixed in a single bed or may be placed in the bed in series, such as by loading the catalysts sequentially in a single layer or placing the catalysts in the reactor as separate layers.

Isomerization catalyst bed 142 may contain the γ-alumina-titania catalyst as disclosed herein. Metathesized effluent 26d may then be processed as discussed above.

Isomerization catalysts according to embodiments disclosed herein may also be useful in other processes where the isomerization catalyst may be exposed to oxygenates. Such processes may include those for isomerizing olefins other than C4 olefins, such as C5, C6, C7, C8, and higher olefins, where the feed stream may include oxygenates that are known to poison conventional basic metal oxide isomerization catalysts.

As described above, embodiments disclosed herein provide catalysts for the dual function of isomerization of 1-butene to 2-butene, dehydration of alcohols to form olefins, and metathesis of 2-butene and ethylene to form propylene, Isomerization catalysts disclosed herein may be a crystalline γ-phase alumina catalyst admixed with titania.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A catalyst useful for the double-bond isomerization of olefins, in the presence of oxygenates, comprising a γ-alumina-titania mixture having:
   a surface area of greater than 200 m$^2$/g;
   from 0.01 wt % to 40 wt % titania;
   wherein the catalyst is resistant to poisoning by oxygenates at oxygenate concentrations in the range from about 100 ppm to about 1000 ppm.

2. The catalyst of claim 1, wherein the catalyst exhibits an increase in isomerization activity in the presence of methanol.

3. The catalyst of claim 1, wherein the catalyst also has activity for the dehydration of alcohols to form olefins.

4. The catalyst of claim 1, wherein the catalyst has a surface area greater than 350 m$^2$/g.

5. A system for the production of olefins in the presence of oxygenates, the system comprising:
   an inlet for receiving an olefin-containing hydrocarbon feed;
   a reaction zone comprising at least one bed of catalyst, the at least one bed of catalyst containing a γ-alumina-titania catalyst, the catalyst having:
   a surface area of greater than 200 m$^2$/g;
   from 0.01 wt % to 40 wt % titania;
   activity for the double bond isomerization of the olefin to form an isomerized olefin product; and
   wherein the catalyst is resistant to poisoning by oxygenates at oxygenate concentrations in the range from 100 ppm to 1000 ppm;
   an outlet for recovering an effluent comprising the isomerized olefin product.

6. The system of claim 5, wherein the catalyst also has activity for the dehydration of alcohols to form olefins.

7. The system of claim 5, wherein the catalyst exhibits an increase in isomerization activity in the presence of methanol.

8. The system of claim 5, the reaction zone further comprising at least one catalyst bed containing a basic metal oxide isomerization catalyst located downstream of the at least one bed of catalyst containing the γ-alumina-titania catalyst.

9. The system of claim 5, the reaction zone further comprising a metathesis catalyst.

10. The system of claim 9, wherein the metathesis catalyst is contained in a bed downstream of the at least one bed of catalyst containing the γ-alumina-titania catalyst.

11. The system of claim 9, wherein the metathesis catalyst is admixed with the γ-alumina-titania catalyst or is admixed with a basic metal oxide isomerization catalyst.

12. A system for the production of olefins in the presence of oxygenates, the system comprising:
   one or more inlets for receiving an olefin and a C2-C6 alcohol;
   a reaction zone comprising at least one bed of catalyst, the at least one bed containing a γ-alumina-titania catalyst, the catalyst having:
   a surface area of greater than 200 m$^2$/g;
   from 0.01 wt % to 40 wt % titania;
   activity for the dehydration of the C2-C6 alcohols to form additional olefins;
   activity for the double bond isomerization of the olefins, provided in the feed or formed in situ from the dehydration of the C2-C6 alcohols, to form an isomerized olefin product; and
   wherein the catalyst is resistant to poisoning by oxygenates at oxygenate concentrations in the range from 100 ppm to 1000 ppm;
   an outlet for recovering an effluent comprising the isomerized olefin product.

13. The system of claim 12, wherein the catalyst exhibits an increase in isomerization activity in the presence of methanol.

14. The system of claim 12, the reaction zone further comprising at least one catalyst bed containing a basic metal oxide isomerization catalyst located downstream of the at least one bed containing the γ-alumina-titania catalyst.

15. The system of claim 12, the reaction zone further comprising a metathesis catalyst.

16. The system of claim 15, wherein the metathesis catalyst is contained in a bed downstream of the bed containing the γ-alumina-titania catalyst.

17. The system of claim 15, wherein the metathesis catalyst is admixed with the γ-alumina-titania catalyst or is admixed with a basic metal oxide isomerization catalyst.

* * * * *